US012799231B2

(12) United States Patent
Wang et al.

(10) Patent No.: US 12,799,231 B2
(45) Date of Patent: Nov. 17, 2026

(54) PROMOTION SYSTEM FOR CELLULAR PROTEIN SYNTHESIS AND USE THEREOF

(71) Applicant: THIRD INSTITUTE OF OCEANOGRAPHY, MNR, Xiamen City (CN)

(72) Inventors: Wanpeng Wang, Xiamen City (CN); Zongze Shao, Xiamen City (CN); Zining Wang, Xiamen City (CN); Bin Zhi, Xiamen City (CN); Xiyan Zhang, Xiamen City (CN)

(73) Assignee: THIRD INSTITUTE OF OCEANOGRAPHY, MNR, Xiamen City (CN)

( * ) Notice: Subject to any disclaimer, the term of this patent is extended or adjusted under 35 U.S.C. 154(b) by 342 days.

(21) Appl. No.: 18/533,116

(22) Filed: Dec. 7, 2023

(65) Prior Publication Data

US 2025/0092161 A1 Mar. 20, 2025

(30) Foreign Application Priority Data

Sep. 20, 2023 (CN) ........................ 202311217734.0

(51) Int. Cl.
*C07K 19/00* (2006.01)
*C12N 9/14* (2006.01)
(Continued)

(52) U.S. Cl.
CPC ................ *C07K 19/00* (2013.01); *C12N 9/14* (2013.01); *C12N 15/113* (2013.01); *C12N 15/67* (2013.01)

(58) Field of Classification Search
CPC ........ C07K 19/00; C07K 14/195; C12N 9/14; C12N 15/113; C12N 15/67; C12N 15/70;
(Continued)

(56) References Cited

PUBLICATIONS

Mekler, Vladimir, Konstantin Kuznedelov, and Konstantin Severinov. "Quantification of the affinities of CRISPR-Cas9 nucleases for cognate protospacer adjacent motif (PAM) sequences." Journal of Biological Chemistry 295.19 (2020): 6509-6517.*
(Continued)

*Primary Examiner* — Robert B Mondesi
*Assistant Examiner* — Synphane L Shelton
(74) *Attorney, Agent, or Firm* — Shih IP Law Group, PLLC

(57) ABSTRACT

The present disclosure belongs to a promotion system for cellular protein synthesis and use thereof, and specifically relates to the technical fields of cell metabolic engineering and synthetic biology. In the present disclosure, a RNA-binding protein (RBP) AbrP is provided. On one hand, the AbrP binds to translation-promoting factors FusA, LepA, and Era separately; on the other hand, the AbrP binds to a characteristic sequence of an sRNA. A complex resulting from the combination of the AbrP and the promoting factor reaches a translation system of a target mRNA under a guidance of the sRNA, thus releasing the translation-promoting factors FusA, LepA, and Era to stimulate and promote the translation. The present disclosure can solve the current urgent need and practical application for a regulatory element or regulatory system in a positive regulatory mode in the cell metabolic engineering or synthetic biology.

5 Claims, 11 Drawing Sheets

Specification includes a Sequence Listing.

(51) Int. Cl.
*C12N 15/113* (2010.01)
*C12N 15/67* (2006.01)

(58) Field of Classification Search
CPC ........ C12N 15/74; C12N 15/79; C12N 15/82; C12N 15/85; C12N 2310/18; C12N 2840/105
See application file for complete search history.

(56) References Cited

PUBLICATIONS

Sonenberg, Nahum, and Alan G. Hinnebusch. "Regulation of translation initiation in eukaryotes: mechanisms and biological targets." Cell 136.4 (2009): 731-745.*
Veluchamy, Alaguraj, Kaian Teles, and Wolfgang Fischle. "CRISPR-broad: combined design of multi-targeting gRNAs and broad, multiplex target finding." Scientific Reports 13.1 (2023): 19717.*
Xu, Benjin, Ling Liu, and Guangtao Song. "Functions and regulation of translation elongation factors." Frontiers in Molecular Biosciences 8 (2022): 816398.*
De Gregorio, Ennio, Thomas Preiss, and Matthias W. Hentze. "Translation driven by an elF4G core domain in vivo." The EMBO journal 18.17 (1999): 4865-4874.*
He, Xiangyun, et al. "Tex, a putative transcriptional accessory factor, is involved in pathogen fitness in *Streptococcus pneumoniae*." Microbial pathogenesis 41.6 (2006): 199-206.*
Verstraeten, Natalie, et al. "The universally conserved prokaryotic GTPases." Microbiology and Molecular Biology Reviews 75.3 (2011): 507-542.*
He, Xiangyun, et al. "Tex, a putative transcriptional accessory factor, is involved in pathogen fitness in *Streptococcus pneumoniae*." Microbial pathogenesis 41.6 (2006): 199-206. (Year: 2006).*

* cited by examiner

SEQUENCE LISTING

```
Sequence total quantity: 11
SEQ ID NO: 1            moltype = AA  length = 778
FEATURE                 Location/Qualifiers
source                  1..778
                        mol_type = protein
                        note = RNA-binding protein (RBP) AbrP
                        organism = synthetic construct
SEQUENCE: 1
MQSIEQIIAQ ELNAQPQQVT AAVALLDEGA TVPFIARYRK EATGGLDDTQ LRNLEERLRY  60
LRELEERREA ILKSIDEQEK LTPELAKAIR EADTKTRLED LYLPYKPKRR TRAQMAREAG  120
LEPLADALLN DPGLDPDSEA AAYLNEEHKI ASAKDALDGA KQILMERFAE NAELLTRMRT  180
FLWERAQIQS RVADGKEEAG AKFRDYFEHQ EALKNIPSHR ALALFRGRNE GVLHVAMVLP  240
EELESAEPHP CVAMVREVAG WRDQGRAADT WLGEVMRWTW KIKLNTHLET ELLGRVRELA  300
EEEAIQVFAR NLKSLLMASP AGPKATMGLD PGLRTGVKVV VVDATGKLLE HTTIFPHVPK  360
NQWAQSLAAL TKLSVKHQVD LVAIGNGTAS RETDKLAGEL VKALKDKQQI QKIMVSEAGA  420
SVYSASELAA REFPELDVSF RGAVSIARRL QDPLAELVKI DPKSIGVGQY QHDVSQVKLS  480
RSLDAVVEDC VNAVGVDVNT ASAPLLARIA GLNSTIAGNI VSFREKNGAF NDRDALKQVP  540
RLGEKTFEQA AGFLRVMNGT NPLDGSAVHP EAYPVVERIA KQHDRPIKDL IGDIPFLKSV  600
KPVEFTDEHF GLPTVTDILG ELEKPGRDPR PEFKAAEFKE GVETLADLKP GMILEGAVTN  660
VTNFGAFVDI GVHQDGLVHV SALADKFVED PHDVVNPGDI VKVKVLEVDQ ARKRISLTMR  720
MDDHHQERQA GQSEGAPAGK GRRGGQRQRG GGNKPAAAPQ GALGAAFAKA LEQKKKRG    778

SEQ ID NO: 2            moltype = DNA  length = 2337
FEATURE                 Location/Qualifiers
source                  1..2337
                        mol_type = other DNA
                        note = RBP AbrP for use in prokaryotic cells
                        organism = synthetic construct
SEQUENCE: 2
atgcagagca tcgaacagat catcgcccag gaactcaacg cccagccgca acaggtgacc  60
gccgccgtgg ccctgctgga cgaaggggcc accgtgccgt ttatcgcccg ttaccggaaa  120
gaggccaccg gcgggctgga tgacacccag ttgcggaacc tggaagagcg gctgcgctac  180
ctgcgcgaac tggaggagcg ccgcgaggcg atcctcaaga gcatcgacga gcaggagaag  240
ctgaccccgg agcttgcaaa ggcgatccgc gaggcggaca ccaagacccg gctcgaggat  300
ctgtatctgc cgtacaagcc caagcgccgc acccgcgcgc agatggcccg cgaggccggc  360
```

-continued ctggagcctc tggcggacgc tctgctgaac gatcccggcc tggacccgga tagcgaggcc 420
gccgcttacc tcaacgaaga acacaagatc gcttccgcca aggacgccct ggacggcgcc 480
aagcagatcc tgatggagcg cttcgccgag aacgccgaac tgctcacccg catgcgcacc 540
ttcctttggg agcgggccca gatccagtcc cgggtggccg acggcaagga agaagcaggc 600
gccaagttcc gcgactactt cgaacaccag gaagcactca agaacattcc cagccaccgt 660
gccctggcgc tgtttcgcgg ccgcaacgaa ggcgtgctgc acgtcgccat ggtgctgccg 720
gaagaactgg aaagcgccga accccatccc tgcgtggcca tggtccgcga agtggccggc 780
tggcgcgatc agggccgcgc cgccgatacc tggctcggcg aggtgatgcg ctggacctgg 840
aagatcaaac tcaacaccca tctggaaacc gaactgctcg gccgcgtgcg cgaactggcc 900
gaggaagagg cgatccaggt gttcgcccgc aacctcaaga gcctgctgat ggcctctccg 960
gcgggtccga aggccaccat gggcctggac ccggggctgc gtaccggggt caaggtggtg 1020
gtggtggacg ctaccggcaa gttgctggaa cacaccacga tttttccgca cgtgccgaaa 1080
aatcagtggg cacagtccct ggcggcgctg accaaactga gcgtcaagca tcaggtggat 1140
ctggtggcga tcggcaacgg caccgccagc cgcgaaaccg acaagctggc cggcgaactg 1200
gtcaaggcgc tcaaggacaa gcagcagatt cagaagatca tggtgtccga ggccggcgcc 1260
tcggtgtact ccgcctccga gctggcggcg cgggaattcc cggaactgga tgtgtccttc 1320
cgcggcgccg tgtccatcgc ccgccgtctg caggacccgc tggcggagtt ggtcaagatc 1380
gacccgaaat ccatcggcgt cggccagtac cagcacgacg tcagccaggt gaagctgtcg 1440
cgctccctgg atgcggtggt ggaagactgc gtgaacgccg tcggcgtgga cgtgaacacc 1500
gccagcgcgc cgctgctggc gcgcatcgcc ggcctcaaca gcaccatcgc cggcaacatc 1560
gtcagcttcc gcgagaagaa cggcgccttc aacgatcgtg acgctctgaa gcaggtgccg 1620
cgtctgggtg aaaagacctt cgaacaggcc gccggcttcc tgcgggtcat gaacggtacg 1680
aacccgctgg acggttccgc tgtgcacccg gaggcctatc cggtggtgga gcggatcgcc 1740
aagcagcacg accgcccgat caaggacctg atcggcgaca tcccgttcct gaagagcgtc 1800
aaaccggtcg agttcactga cgagcatttc ggtctgccca ccgtcaccga catccttggc 1860
gagctggaaa agccgggccg cgacccgcgc ccggaattca aggcggcgga gttcaaggaa 1920
ggggtggaaa ccctggccga cctgaagccg ggcatgatcc tggaaggcgc ggtaaccaac 1980
gtcaccaact ttggcgcctt cgtcgacatc ggcgtgcatc aggacggtct ggtgcacgtg 2040
tcggcgctgg ccgacaaatt cgtcgaggat ccccatgatg tggtcaaccc cggcgacatc 2100
gtcaaagtga aagtgctgga agtggatcag gcgcgcaaac gcatcagcct gaccatgcgt 2160
atggacgatc accaccagga gcgtcaggct ggtcagagcg agggcgcacc ggcgggcaag 2220
ggccggcggg gcggccagcg gcagcgtggt ggcggcaaca aaccggcggc ggcaccacag 2280
ggcgccctgg gcgcggcttt cgccaaggcc ctggagcaaa agaagaagcg cggctaa 2337

SEQ ID NO: 3 moltype = DNA length = 1953
FEATURE Location/Qualifiers
source 1..1953
mol_type = other DNA
note = RBP AbrP for use in eukaryotic cells
organism = synthetic construct
SEQUENCE: 3
atgcagagca tcgagcagat tatcgcccag gagctgaatg ctcagccaca gcaggtcacc 60
gcagctgtgg ctctgctgga tgaaggcgct accgtgcctt tcattgccag atacagaaag 120
gaggcaaccg gtggcctgga tgacactcag ctgaggaacc tggaggagag actgagatac 180
ctgagagagc tggaggagcg cagagaggcc atactgaaat ccattgacga gcaggagaaa 240
ctgacccccg agctggccaa agccatccgc gaagctgaca caaagacccg gctggaagat 300
ttgtatctgc cttacaagcc caaacggaga acaagggcac agatggcccg cgaggctggc 360
ctggagccac tggccgatgc cctgctgaat gaccctggac tggaccctga ctccgaggcc 420
gcggcctacc tgaacgagga gcacaagata gcctctgcca aggacgccct ggacggggcc 480
aagcagattc tgatggaacg cttcgccgag aacgccgagc tgctgacccg gatgagaacc 540
ttcctatggg agcgggctca gattcagtcc agggtggcag atggcaagga ggaagccgga 600
gccaaattcc gcgactattt tgagcaccag gaggccctga agaatatccc aagccatcgc 660
gccctggctc tctttagagg aagaaacgag ggggtcctgc acgtggccat ggtgctgccc 720
gaggagctgg agagcgctga acctcaccca tgtgtggcca tggtgcgcga ggtggccggg 780
tggagggacc aggggagggc cgccgataca tggcttggcg aggtgatgag gtggacctgg 840
aaaatcaaac tgaacactca tctggaaacc gagctgctcg gccgggttag ggagctggcc 900
gaggaggagg ccatccaggt gtttgcccgg aatctgaaaa gcctgctgat ggcctctccc 960
gccggcccaa aagccaccat gggactggac cctggtctga ggacaggggt taaagtggtg 1020
gtggtcgacg ccacaggcaa gctgctcgag cacaccacta tcttccccca cgtgcctaag 1080
aaccagtggg cccagtctct ggccgctctg accaagctga gcgtgaaaca ccaggtggac 1140
ctggtggcta tcgggaacgg tactgcctcc agagagaccg ataaactggc cggcgagctg 1200
gttaaggccc tgaaagataa gcagcagatc cagaaaatca tggtgtccga ggcaggggct 1260
tccgtgtaca gcgcctccga gctggccgcc cgggaatttc ctgagctgga cgtgtctttc 1320
agaggcgccg tgagcatagc cagaagactg caggaccctc tggctgaact ggtgaagatc 1380
gatcccaaga gcatcggggt gggccagtac cagcacgatg tgagccaggt gaagctgagt 1440
cggtctctgg acgccgtggt ggaggactgt gtgaatgccg tgggcgtgga cgtgaacacc 1500
gcctctgccc ccctgctggc cagaatcgcc ggcctgaata gcaccattgc cggcaacatt 1560
gtgtctttcc gcgaaaagaa cggagccttc aacgacagag atgccctgaa gcaggtgccc 1620
agactgggcg agaagacatt tgagcaggcc gccgggttcc tgcgggtgat gaatggcacc 1680
aatcccctgg atggctctgc cgtgcaccct gaagcctacc ccgtggtcga aaggatcgcc 1740
aagcagcatg atcgacccat taaggatctg attggggata tccctttcct gaaatctgtg 1800
aagcccgtgg agttcacaga tgagcacttc ggactgccaa ccgtgactga cattctcgga 1860
gagctggaga agcccggccg ggacccccgc ccagagttca aagccgccga gttcaaggag 1920
ggcgtggaga cactggcaga cctgaaacca tga 1953

SEQ ID NO: 4 moltype = RNA length = 20
FEATURE Location/Qualifiers
source 1..20
mol_type = other RNA -continued

```
                        note = A binding part of the RBP AbrP that binds to sRNA
                        organism = synthetic construct
SEQUENCE: 4
gggaagcdgy dyykgstggc                                                20

SEQ ID NO: 5            moltype = RNA  length = 51
FEATURE                 Location/Qualifiers
source                  1..51
                        mol_type = other RNA
                        note = ppc-gRNA
                        organism = synthetic construct
SEQUENCE: 5
gggagcagct ctggctggca ttagactgta ttgaaaggcg aagaactgcc a             51

SEQ ID NO: 6            moltype = RNA  length = 51
FEATURE                 Location/Qualifiers
source                  1..51
                        mol_type = other RNA
                        note = gpd-gRNA
                        organism = synthetic construct
SEQUENCE: 6
gggagcagct ctggctggca ttagactgta tacactgctc aaaagcacat t             51

SEQ ID NO: 7            moltype = RNA  length = 51
FEATURE                 Location/Qualifiers
source                  1..51
                        mol_type = other RNA
                        note = gpp-gRNA
                        organism = synthetic construct
SEQUENCE: 7
gggagcagct ctggctggca ttagactgta tttttaggca aggtttcatg g             51

SEQ ID NO: 8            moltype = RNA  length = 51
FEATURE                 Location/Qualifiers
source                  1..51
                        mol_type = other RNA
                        note = bmsq-gRNA
                        organism = synthetic construct
SEQUENCE: 8
gggagcagct ctggctggca ttagactgta tacatttttt attccaatta g             51

SEQ ID NO: 9            moltype = RNA  length = 51
FEATURE                 Location/Qualifiers
source                  1..51
                        mol_type = other RNA
                        note = pgsq-gRNA
                        organism = synthetic construct
SEQUENCE: 9
gggagcagct ctggctggca ttagactgta ttacttatgt atgagggcaa t             51

SEQ ID NO: 10           moltype = RNA  length = 51
FEATURE                 Location/Qualifiers
source                  1..51
                        mol_type = other RNA
                        note = scsq-gRNA
                        organism = synthetic construct
SEQUENCE: 10
gggagcagct ctggctggca ttagactgta tttttatttg attttaaggg c             51

SEQ ID NO: 11           moltype = RNA  length = 51
FEATURE                 Location/Qualifiers
source                  1..51
                        mol_type = other RNA
                        note = glnA-gRNA
                        organism = synthetic construct
SEQUENCE: 11
gggagcagct ctggctggca ttagactgta ttctttcacg atcctttcac c             51
```

PROMOTION SYSTEM FOR CELLULAR PROTEIN SYNTHESIS AND USE THEREOF

CROSS REFERENCE TO RELATED APPLICATION

This patent application claims the benefit and priority of Chinese Patent Application No. 2023112177340, filed with the China National Intellectual Property Administration on Sep. 20, 2023, the disclosure of which is incorporated by reference herein in its entirety as part of the present application.

FIGURE SELECTED FOR PUBLICATION

FIG. 2.

REFERENCE TO SEQUENCE LISTING

A computer readable XML file entitled "GWP20220801010_seglist", that was created on Nov. 10, 2023, with a file size of about 17,834 bytes, contains the sequence listing for this application, has been filed with this application, and is hereby incorporated by reference in its entirety.

TECHNICAL FIELD

The present disclosure belongs to the technical fields of cell metabolic engineering and synthetic biology, and specifically relates to a promotion system for cellular protein synthesis and use thereof.

BACKGROUND

Over the past 30 years, metabolic engineering has emerged as a powerful tool to improve cell performance and enable sustainable biomanufacturing production of compounds. However, changes in metabolic pathways and the introduction of exogenous proteins increase the demand for cellular resources and disrupt the normal physiological balance of cells. Overexpression of pathway proteins can hinder cell growth and thus reduce productivity; simply reducing the expression level of pathway enzymes may form a bottleneck in the reaction pathway, thereby limiting yield and titer. Therefore, more refined regulation of pathways is needed to achieve a balance between cell growth and product synthesis.

Metabolic engineering improves cellular synthetic capabilities by modifying the metabolic network of chassis cells, while synthetic biology aims to create new cellular functions and/or reprogram existing cellular functions based on mechanical engineering principles. Artificially designed and synthesized regulatory elements theoretically have less interaction with the endogenous transcriptional regulatory network of chassis cells and are orthogonal. Accordingly, in the future, it is necessary to construct predictable, orthogonal, and quantitatively-controllable gene circuits based on standardized characterization elements, hoping to achieve "ground-up" balanced expression of genes in cells. In addition, the development of synthetic biology allows researchers to control cell phenotypes at the temporal or spatial level through intelligent methods, but there are still poor level of control and flexibility yet. As a result, the transformation technology of cell regulation should also develop in the direction of programmability, multi-target, and automatic feedback control in the future.

Currently, synthetic biology can achieve multi-level coordinated regulation of metabolic networks, significantly improving biosynthetic capabilities. However, it needs to be emphasized that achieving precise and effective balance of bacterial physiology and efficient synthesis of target compounds is the ultimate goal pursued by industrial microbial technology. Metabolic engineering has stringent standards for the economics of production performance. Compared with general synthetic biology research, the regulatory tools used in actual metabolic engineering show more stringent restrictions on the loading and toxicity of components. Although the library of synthetic biology regulation tools has been enriched in recent years, the currently available switches or regulation tools are still extremely limited compared to the diverse application scenarios and evolving technical needs of metabolic engineering. It is necessary to further optimize and develop new intelligent dynamic control systems oriented to metabolic engineering applications. With the development of synthetic biology and artificial intelligence technology, biomanufacturing may have a major impact on many fields, while there may be more urgent demand for new expression components and control methods. In addition, the current RNA regulatory elements regulating metabolic pathways are all in negative regulatory modes at the transcription or translation level. At present, metabolic engineering or synthetic biology has an urgent need for regulatory elements in positive regulatory modes and has diverse application requirements.

SUMMARY

In order to solve the current urgent need and practical application of regulatory elements or regulatory systems in positive regulatory modes in cell metabolic engineering or synthetic biology, a purpose of the present disclosure is to provide a promotion system for cellular protein synthesis and use thereof.

The present disclosure provides a RNA-binding protein (RBP) AbrP, where the RBP AbrP has an amino acid sequence shown in SEQ ID NO: 1.

The present disclosure further provides use of RBP AbrP in promoting recombinant protein translation.

Preferably, the recombinant protein translation includes expression of an exogenous protein in a host cell.

Preferably, the host cell includes a prokaryotic cell and/or a eukaryotic cell.

The present disclosure further provides an mRNA translation-promoting complex based on sRNA targeting, where the mRNA translation-promoting complex includes a AbrP combined with a translation-promoting factor, and the RBP AbrP has an amino acid sequence shown in SEQ ID NO: 1.

Preferably, the translation-promoting factor includes FusA, LepA, and Era.

The present disclosure further provides an AbrP protein translation-promoting system, including the mRNA translation-promoting complex.

The present disclosure further provides use of the AbrP protein translation-promoting system in metabolic engineering regulation of a prokaryotic chassis cell.

The present disclosure further provides use of the AbrP protein translation-promoting system in metabolic engineering regulation of a eukaryotic chassis cell.

The present disclosure further provides use of the AbrP protein translation-promoting system in metabolic engineering and/or biosynthesis of animal and plant cells.

Beneficial effects: the present disclosure provides a RBP AbrP, an mRNA translation-promoting complex based on sRNA targeting, and a corresponding AbrP protein translation-promoting system. It is confirmed by the examples that the AbrP protein binds to translation-promoting factors FusA, LepA, and Era separately and then promotes translation of a target mRNA. The translation-promoting process is mainly characterized by promoting a stability of bacterial ribosomes, promoting an initiation process of translation, and promoting an elongation process of translation.

In the present disclosure, a bacterial translation-promoting molecular system for a target mRNA based on sRNA targeting is discovered and verified for the first time. A core protein of this system is a novel RBP AbrP On one hand, the AbrP binds to translation-promoting factors FusA, LepA, and Era separately; on the other hand, the AbrP binds to a characteristic sequence of an sRNA. A complex resulting from the combination of the AbrP and the promoting factor reaches a translation system of a target mRNA under a guidance of the sRNA, thus releasing the translation-promoting factors FusA, LepA, and Era to stimulate and promote the translation.

In the examples of the present disclosure, representative strains of hydrocarbon-degrading bacteria (*Alcanivorax*) widely distributed in the ocean are used as research materials. It is discovered and confirmed that the novel bacterial RBP AbrP combines with multiple sRNAs to promote the translation of multiple target genes involved in hydrocarbon metabolism in a sensing and signal transduction system, an uptake transport system, a chemotaxis and movement system, a regulatory and degradation system, and a secretion system of bacteria. Sequence analysis has confirmed that multiple sRNAs that bind to the RBP AbrP have a conserved sequence region of 20 nt to 25 nt, and it is also verified that this conserved sequence region binds to an S1 domain of the AbrP (FIGS. 1A-C). Through a series of biochemical and molecular biology experiments such as CoIP-MS experiments, bacterial two-hybrid verification, dual-plasmid protein translation verification experiments, quantitative mass spectrometry technology, bacterial translation group (Ribo-seq) technology, surface plasmon resonance (SPR) technology, and bacterial ribosome in vitro translation experiments, it is confirmed that the AbrP binds to three types of non-classical GTP hydrolase translation-promoting factors (FusA, LepA, and Era) in bacteria and promotes the translation of target mRNAs (FIG. 2). The translation-promoting process is mainly characterized by promoting a stability of bacterial ribosomes, promoting an initiation process of translation, and promoting an elongation process of translation. Therefore, a bacterial translation-promoting molecular system based on sRNA targeting of the target mRNA is discovered and verified for the first time in the present disclosure. A core protein of this system is a novel RBP AbrP. On one hand, the AbrP binds to the translation-promoting factors FusA, LepA, and Era separately (structural analysis confirms that AbrP mainly binds to a GTPase hydrolase domain part of the translation-promoting factors FusA, LepA, and Era); on the other hand, the AbrP binds to a characteristic sequence of an sRNA. A complex resulting from the combination of the AbrP and the promoting factor reaches a translation system of a target mRNA under a guidance of the sRNA, thus releasing the translation-promoting factors FusA, LepA, and Era to stimulate and promote the translation (FIG. 2).

BRIEF DESCRIPTION OF THE DRAWINGS

FIG. 1A: a left figure is a schematic diagram of a spatial structure of the AbrP, and sRNA-binding conserved residues R718, H683, F668, and F671 show green; a right figure is a close-up of the arrangement of conserved residues in a structurally-related S1 domain of the AbrP; and FIG. 1B: a schematic diagram of the model of a binding cleft between the sRNA and S1 domain; FIG. 1C: surface representation showing primary sequence conservation as assigned by the ConSurf server, conservation is indicated as a gradient from black (high) to white (low), in contrast to the view shown here, minimal conservation is observed on the opposite face of the S1 domain;

DETAILED DESCRIPTION OF THE EMBODIMENTS

The present disclosure provides a RNA-binding protein (RBP) AbrP, where the RBP AbrP has an amino acid sequence shown in SEQ ID NO: 1. The RBP AbrP can be applied to prokaryotic and eukaryotic cells. However, when applied in prokaryotic cells, an encoding gene of the RBP AbrP is preferably shown in SEQ ID NO: 2; when applied to eukaryotic cells, the encoding gene is preferably shown in SEQ ID NO: 3.

In the present disclosure, the biological species distribution of the AbrP protein shown in SEQ ID NO: 1 is analyzed.

Figure 3:
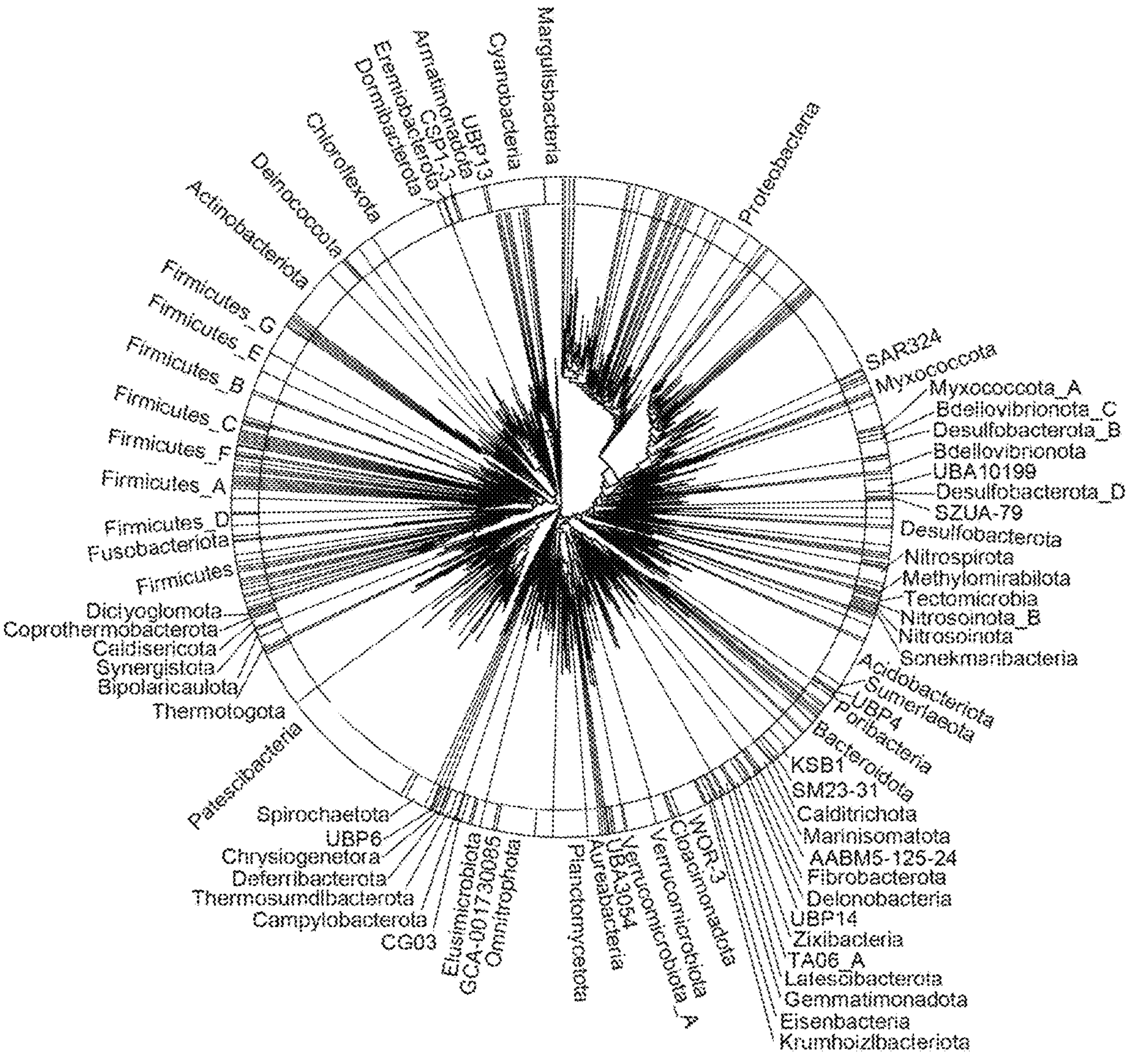
FIG. 3 shows a schematic diagram of distribution of the bacterial protein AbrP in a bacterial domain (with an amino acid sequence similarity of >70%)

The results show that AbrP protein is widely distributed in bacterial taxa (FIG. 3), such as *Proteobacteria, Myxococcota, Desulfobacterota, Nitrospirota, Acidobacteriota, Bacteroidota*, and *Firmicutes*; AbrP-like protein sequences are retrieved from not less than 50% of bacterial genomes (Annotree website, amino acid sequence similarity of >50%). AbrP-like protein sequences have been retrieved from the genomes of chassis cells using synthetic biology, such as *E. coli, Bacillus subtilis*, and *Corynebacterium glutamicum*, but the similarity is around 40% to 60%. However, the AbrP-like protein sequences have not been found in archaea, fungi, and eukaryotic cells. This shows the possibility that some chassis cells have the AbrP protein translation-promoting system of *Alcanivorax*. A dual-plasmid protein translation verification experiment is conducted in *E. coli* cells. The combination of the AbrP protein of *Alcanivorax* and sRNA significantly promoted the translation process and efficiency of the target mRNA (a control is as no AbrP protein or expression of sRNA). This shows that the AbrP protein translation-promoting system has a strong potential to work in chassis cells using synthetic biology. The AbrP protein of *Alcanivorax* and synthetic sRNA (i.e. gRNA, 25 nt AbrP protein-binding conserved sequence+40 nt target mRNA complementary sequence) were adopted to promote the translation of target mRNA in vitro (ribosome in vitro translation experiment) or in vivo (*E. coli*) and efficiency testing. The results have showed that AbrP protein and synthetic sRNA also significantly promoted the translation of target mRNA, whether in vivo or in vitro. This shows that the AbrP protein translation-promoting system has the flexibility and designability to regulate targets.

Figure 1A:
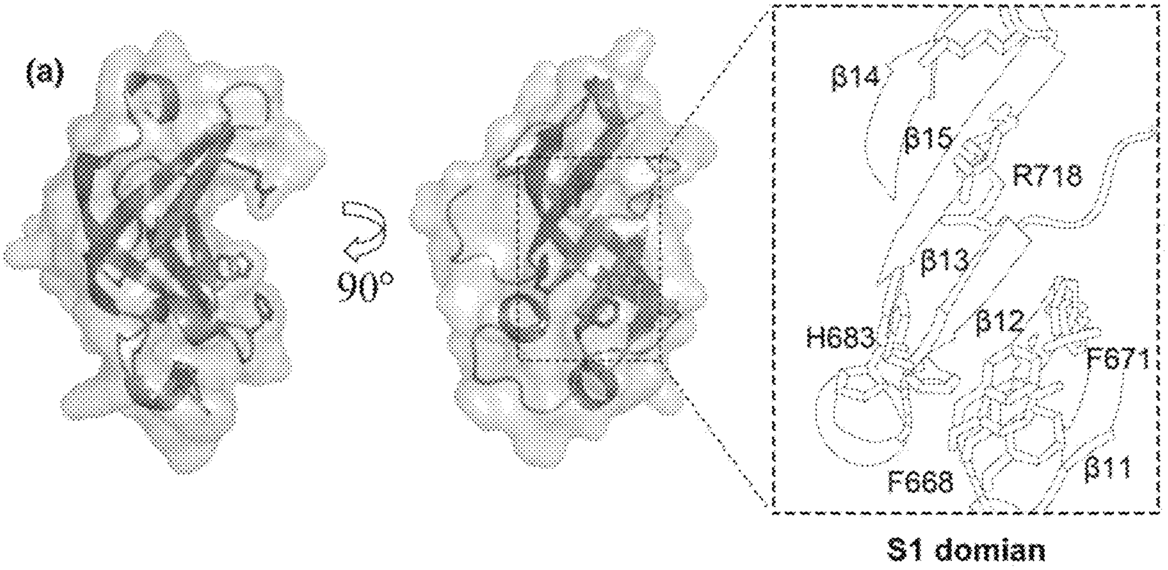
FIGS. 1A-C show schematic diagrams of a bacterial protein AbrP structure and a small-molecule RNA-binding domain; where
Figure 1B:
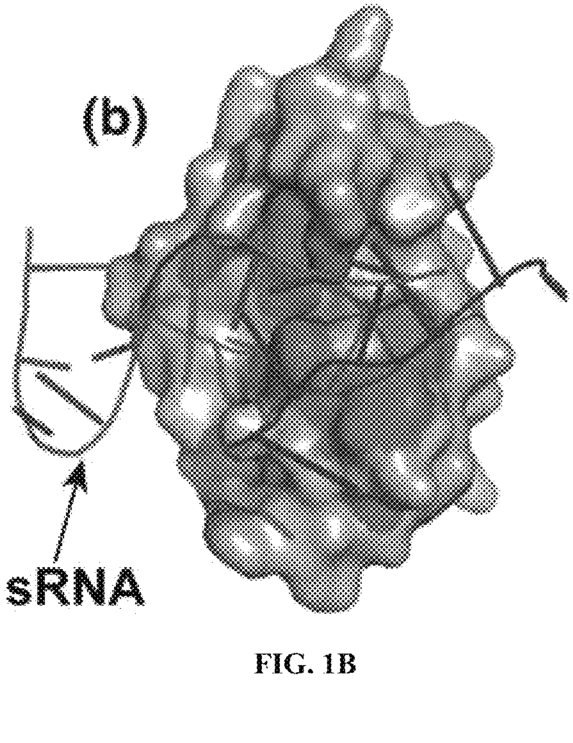
Figure 1C:
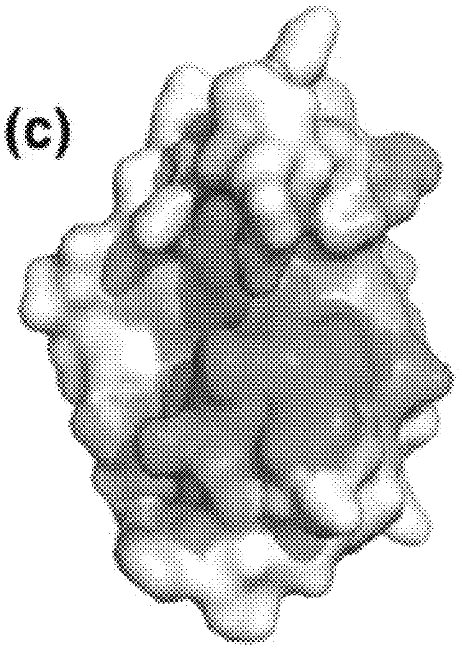

In the present disclosure, the RBP AbrP is preferably derived from a representative strain of hydrocarbon-degrading bacteria (*Alcanivorax*). It is discovered and confirmed that the novel bacterial RBP AbrP combines with multiple sRNAs to promote the translation of multiple target genes involved in hydrocarbon metabolism in a sensing and signal transduction system, an uptake transport system, a chemotaxis and movement system, a regulatory and degradation system, and a secretion system of bacteria. Sequence analysis has confirmed that multiple sRNAs that bind to the RBP AbrP have a conserved sequence region of 20 nt to 25 nt, and it is also verified that the conserved sequence region binds to an S1 domain of the AbrP (FIG. 1). A binding part of the RBP AbrP that binds to sRNA has a sequence preferably shown in SEQ ID NO: 4: GGGAAGCDGY DYYKGSUGGC. The sRNA preferably needs to design a specific sequence based on different regulatory targets (mRNA), and the specific sequence and the sequence of the binding part constitute a similar guide RNA.

The present disclosure further provides use of the RBP AbrP in promoting recombinant protein translation.

In the present disclosure, the recombinant protein translation includes preferably expression of an exogenous protein in a host cell, and the host cell preferably includes a prokaryotic cell and/or a eukaryotic cell. The prokaryotic cell preferably includes *E. coli, Bacillus subtilis*, and *Corynebacterium glutamicum*. The eukaryotic cell preferably includes fungi, human tumor cells HeLa cells, animal cells, and plant cells, and the fungi preferably include *Saccharomyces cerevisiae* and filamentous fungi.

The present disclosure further provides an mRNA translation-promoting complex based on sRNA targeting, where the mRNA translation-promoting complex includes a RBP AbrP combined with a translation-promoting factor, and the RBP AbrP has an amino acid sequence shown in SEQ ID NO: 1.

In the present disclosure, the translation-promoting factor includes preferably FusA, LepA, and Era.

The present disclosure further provides an AbrP protein translation-promoting system, including the mRNA translation-promoting complex.

Figure 2:
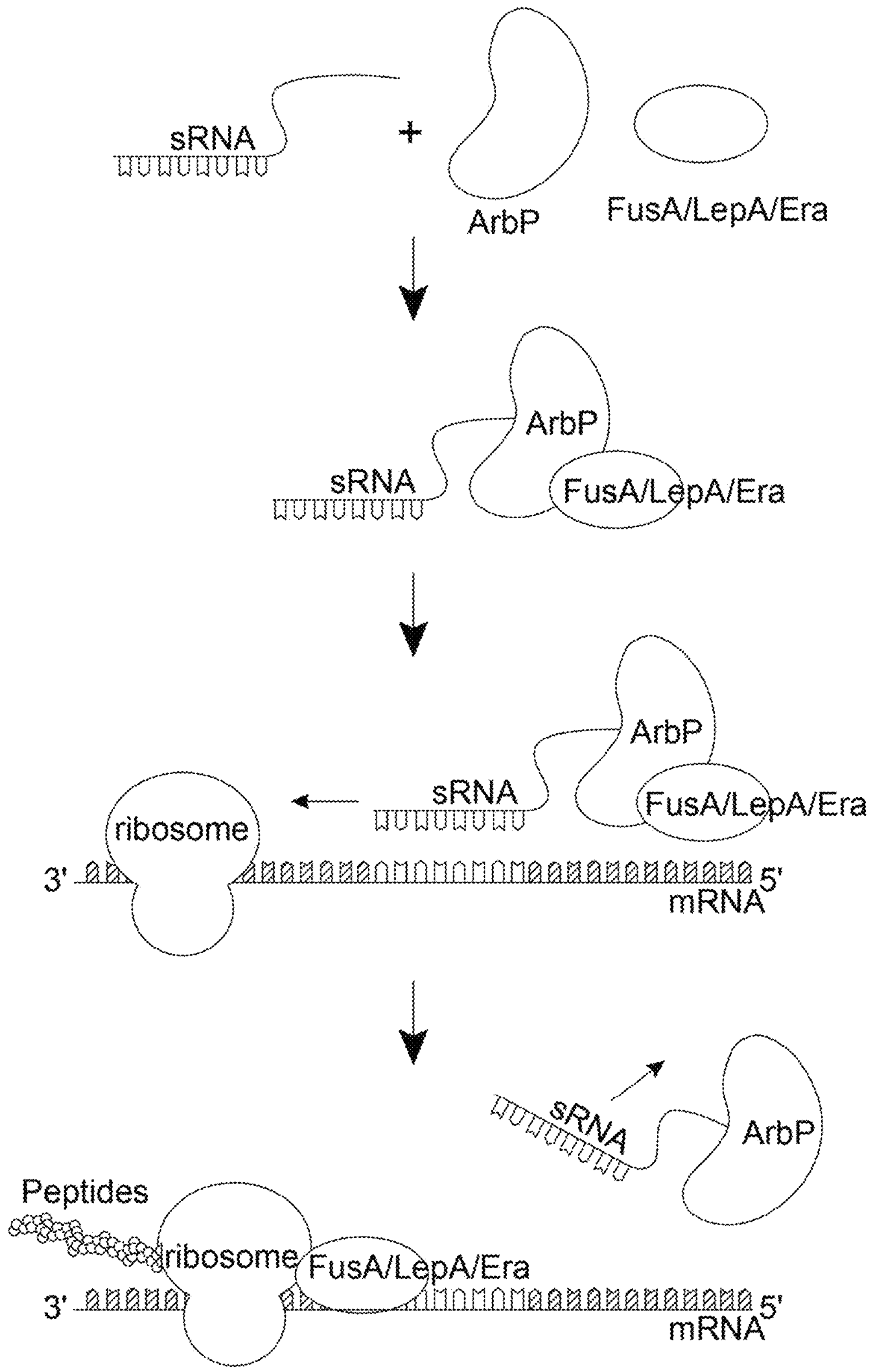
FIG. 2 shows a schematic diagram illustrating the bacterial protein AbrP promoting the translation of a target mRNA.

In the examples of the present disclosure, through a series of biochemical and molecular biology experiments such as CoIP-MS experiments, bacterial two-hybrid verification, dual-plasmid protein translation verification experiments, quantitative mass spectrometry technology, bacterial translation group (Ribo-seq) technology, surface plasmon resonance (SPR) technology, and bacterial ribosome in vitro translation experiments, it is confirmed that the AbrP binds to three types of non-classical GTP hydrolase translation-promoting factors (FusA, LepA, and Era) in bacteria and promotes the translation of target mRNAs (FIG. 2). The translation-promoting process is mainly characterized by promoting a stability of bacterial ribosomes, promoting an initiation process of translation, and promoting an elongation process of translation. A core protein of this system is a novel RBP AbrP. On one hand, the AbrP binds to the translation-promoting factors FusA, LepA, and Era separately (structural analysis confirms that AbrP mainly binds to a GTPase hydrolase domain part of the translation-promoting factors FusA, LepA, and Era); on the other hand, the AbrP binds to a characteristic sequence of an sRNA. A complex resulting from the combination of the AbrP and promoting factor reaches a translation system of a target mRNA under a guidance of the sRNA, thus releasing the translation-promoting factors FusA, LepA, and Era to stimulate and promote the translation (FIG. 2).

In the present disclosure, the AbrP protein translation-promoting system developed in the present disclosure becomes a metabolic network regulatory element in chassis cells of synthetic biology, and also becomes an important tool for studying gene expression regulation in molecular biology and cell biology.

The present disclosure further provides use of the AbrP protein translation-promoting system in metabolic engineering regulation of a prokaryotic chassis cell.

In the present disclosure, the use is preferably the same as the above, and is not repeated here.

The present disclosure further provides use of the AbrP protein translation-promoting system in metabolic engineering regulation of a eukaryotic chassis cell. In the present disclosure, the use is preferably the same as the above, and is not repeated here.

The present disclosure further provides use of the AbrP protein translation-promoting system in metabolic engineering and/or biosynthesis of animal and plant cells. In the present disclosure, the use is preferably the same as the above, and is not repeated here.

In order to further illustrate the present disclosure, the promotion system for cellular protein synthesis and the use thereof provided by the present disclosure are described in detail below with reference to the accompanying drawings and examples, but the accompanying drawings and the examples should not be construed as limiting the protection scope of the present disclosure.

Figure 4:
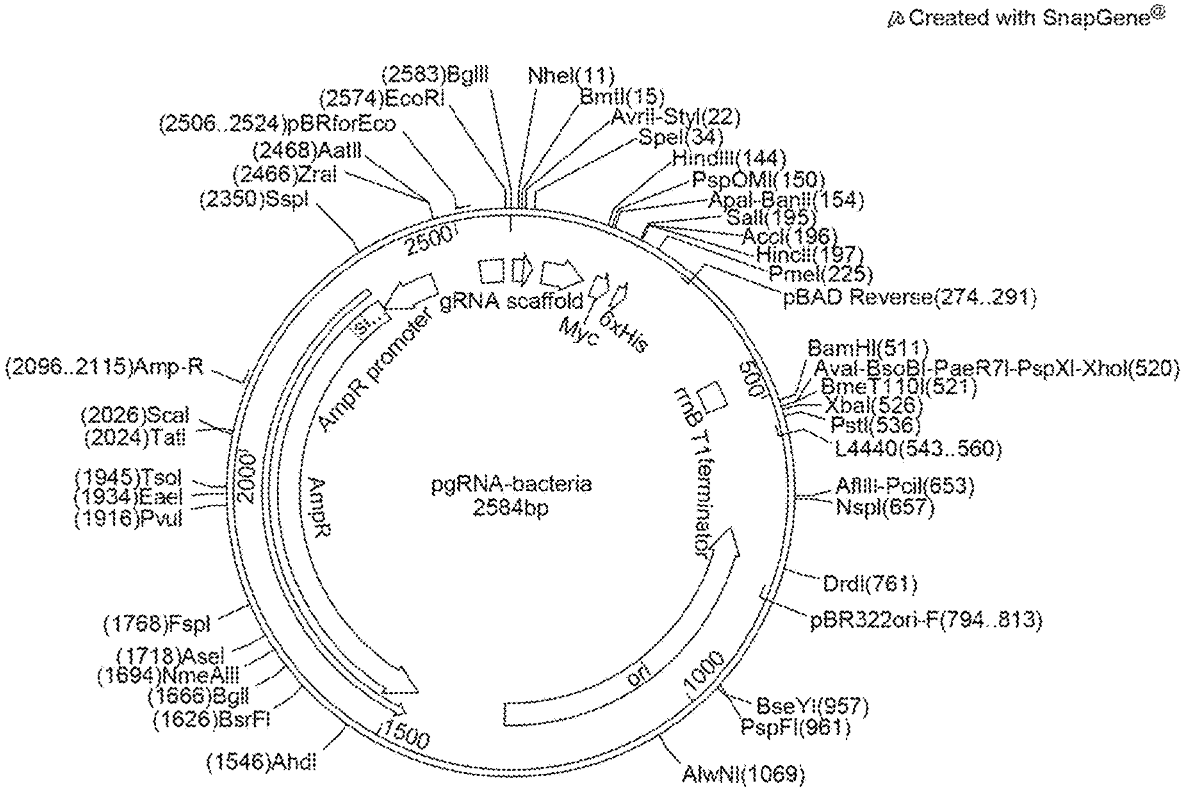
FIG. 4 shows a plasmid map of a bacterial expression vector pgRNA.

Example 1 Construction of a Promotion System for Protein Synthesis in Bacteria and Yeast 1.1. A bacterial expression vector pgRNA (FIG. 4) could be used to realize the simultaneous expression of multiple gRNAs in bacteria (such as *E. coli, Coryne-*

Figure 5:
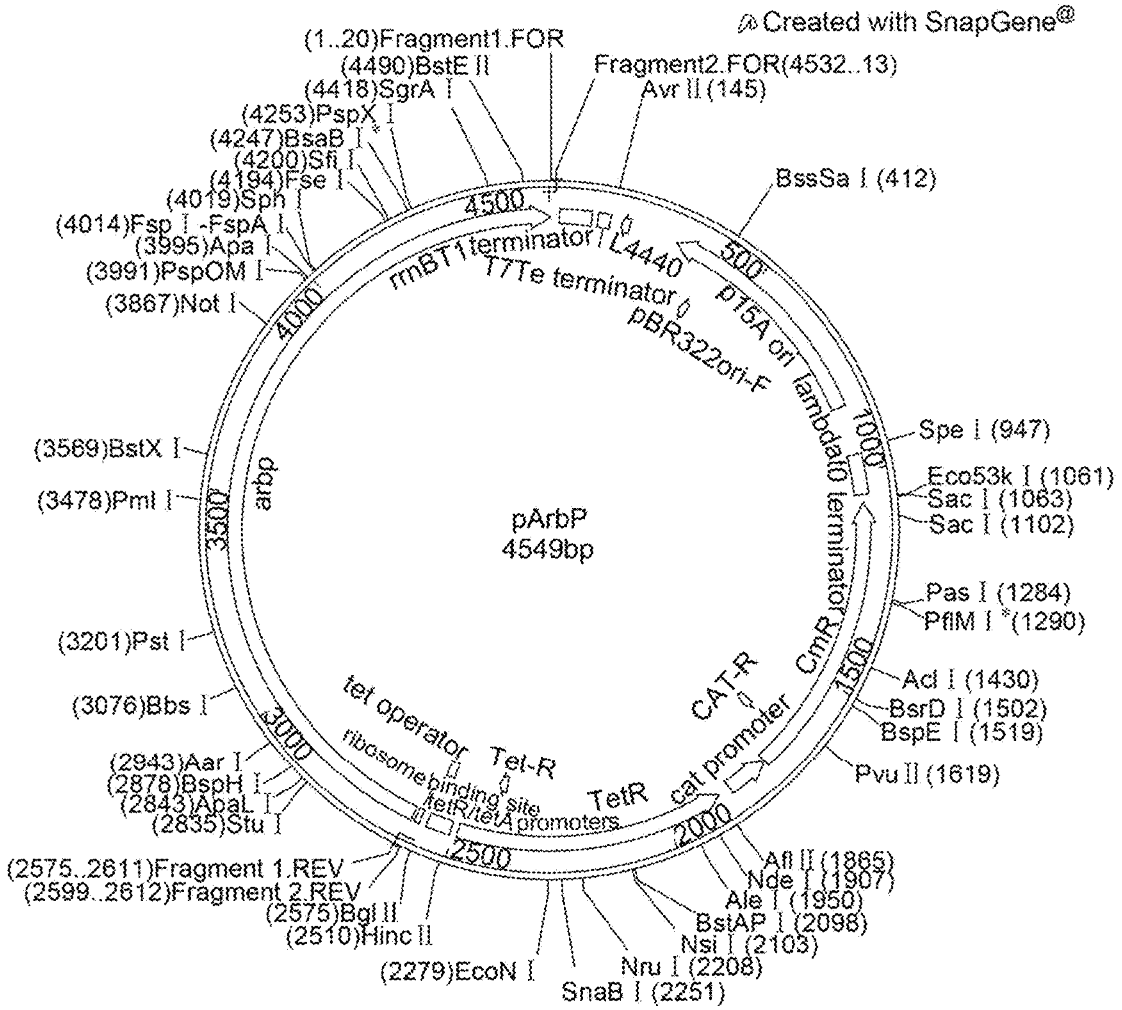
FIG. 5 shows a plasmid map of a bacterial expression vector pCarbP for ArbP protein.

*bacterium glutamicum*, and *Bacillus subtilis*); a pCarbP vector was modified to constitutively express the ArbP protein in *E. coli* (FIG. 5).

1.2. Design and synthesis of gRNA and construction of vector

The *E. coli* had a key gene for succinic acid synthesis, namely a phosphoenolpyruvate carboxylase gene (ppc, NC_000913.3); a targeting gRNA was designed at the +465 position of the CDS interval of the ppc gene, and named as ppc-gRNA, with a sequence shown in SEQ ID NO: 5.

A cell factory of metabolic engineering of 1,3-propanediol-producing *E. coli* was derived from a glycerol-3-phosphate dehydrogenase gene (gpd, NC_001139.9) and a glycerol-3-phospholipase gene (gpp, NC 001146.8) of *Saccharomyces cerevisiae*; a targeting gRNA was designed at the +311 position of the CDS interval of the gpd gene, and named as gpd-gRNA, with a sequence shown in SEQ ID NO: 6; a targeting gRNA was designed at the +141 position of the CDS interval of the gpp gene, and named as gpp-gRNA, with a sequence shown in SEQ ID NO: 7.

There were 3 squalene synthase (SQS) genes from different sources in a cell factory of squalene-producing *Bacillus subtilis*: BmSQS (CP001982.1), PgSQS (KJ939264.1), and ScSQS (U00030.1); a targeting gRNA was designed at the +61 position of the CDS interval of the BmSQS gene, and named as bmsq-gRNA, with a sequence shown in SEQ ID NO: 8; a targeting gRNA was designed at the +121 position of the CDS interval of the PgSQS gene, and named as pgsq-gRNA, with a sequence shown in SEQ ID NO: 9; a targeting gRNA was designed at the +201 position of the CDS interval of the ScSQS gene, and named as scsq-gRNA, with a sequence shown in SEQ ID NO: 10.

There was a glutamine synthetase gene (glnA, AF005635) in a cell factory of L-glutamic acid-producing *Corynebacterium glutamicum*; a targeting gRNA was designed at the +421 position of the CDS interval of the GlnA gene, and named as glnA-gRNA, with a sequence shown in SEQ ID NO: 11.

The synthesized gRNA was ligated into the vector pgRNA according to a method in "*Molecular Biology Experimental Technology*" to form gRNA expression vectors, which were named as ppc-pgRNA and gpd-pgRNA in sequence.

1.3. Preparation of competent cells and transformation of bacteria 1.3.1. *E. coli* W3110 electroporated competent cells were prepared according to the method in "*Molecular Biology Experimental Technology*". A pCas9-CR4 plasmid was transformed into the competent cells.

1.3.2. Preparation and transformation of *Bacillus subtilis* competent cells:

Preparation of Reagents

Preparation of LB medium: 1% (W/V) tryptone, 0.5% (W/V) yeast extract, and 1% (W/V) sodium chloride were sterilized at 121 °C for 15 min.

Preparation of GM medium (growth medium): tryptone 1% (W/V), yeast extract 0.5% (W/V), NaCl 0.5% (W/V), hydrolyzed casein 0.2% (W/V) V), 500 mM sorbitol, 500 mM glucose, 50 mM $K_2HPO_4$, and 50 mM $KH_2PO_4$ were sterilized at 115 °C for 15 min.

Preparation of cell wall weakening agent (WA solution Ox): 5% (W/V) glycine, 10% (W/V) serine, and 5 mmol DTT were used. The glycine and serine were filtered and sterilized using a 0.22 μm filter membrane, and the DTT was sterilized at 121 °C for 15 min.

Preparation of WB buffer (electric shock buffer): 500 mM trehalose, 500 mM sorbitol, 500 mM mannitol, 15 mM $MgCl_2$, 0.5 mM $K_2HPO_4$, 0.5 mM $KH_2PO_4$, and 10% glycerol were mixed, a resulting mixture was adjusted to a pH value of 7.2, and sterilized at 121 °C for 15 min. 0.5% (W/V) 500 mM sorbitol and 350 mM mannitol were added, and sterilized at 121 °C for 15 min.

Preparation of RM medium (resuscitation medium): tryptone 1% (W/V), yeast extract 0.5% (W/V), NaCl 0.5% (W/V), sorbitol 500 mM, and mannitol 350 mM were sterilized at 121 °C for 15 min.

Preparation of *Bacillus subtilis* Competent Cells

1. A single clone of *Bacillus subtilis* was cultured overnight in 2 mL LB medium for 12 h to 14 h at 32 °C and 200 rpm.
2. 400 μL of a resulting culture in step (1) was inoculated into 40 mL of GM medium, and cultured at 32 °C and 200 rpm until $OD_{600}$=0.6.
3. A cell wall weakening agent was added, where final concentrations of the glycine, serine, and DTT were 0.5% (W/V), 1% (W/V), and 0.5 mmol, respectively, and culturing was continued at 37 °C and 200 rpm until $OD_{600}$=0.9.
4. The cells were kept in an ice bath for 10 min, centrifuged to collect *Bacillus subtilis* cells (10,000 g, 4 °C), washed 3 times with pre-cooled WB buffer, and finally resuspended in 100 μL of WB buffer, quickly-frozen in liquid nitrogen, and stored at −80 °C.

Electric Shock Conversion:

1. The *Bacillus subtilis* strain stored at −80 °C was melted naturally on ice. After melting, 100 ng of the plasmid to be transformed was added, and then electric shock was conducted after 5 min of ice bath.
2. A system in step (1) was transferred to a 0 °C pre-cooled electric shock cup (1 mm), and subjected to electric shock with an electrorotator (at voltage 20 kV/cm, capacitance 25 μF, and resistance 200Ω, conducting 1 time for 5 ms).
3. After the electric shock conversion was completed, heat shock was conducted at 30 °C for 5 min.
4. 1 mL of RM medium was added and the cells were incubate at 37 °C for 3 h to 6 h, then spread on an LB plate containing corresponding antibiotics.

1.3.3. Preparation and transformation of electroporated competent cells of *Corynebacterium glutamicum:*

1) Preparation of competent cells: the *Corynebacterium glutamicum* stored at −80 °C was taken out, a small amount of bacterial liquid was collected and cultured in streaks on a solid medium LBHIS.

(1) A ring of seeds of *Corynebacterium glutamicum* was inoculated into a seed medium, and cultured overnight at 200 rpm and 30 °C.

(2) The seeds were transferred into 100 mL medium at a ratio of 10% to make the initial cell OD=0.3, and cultured at 200 rpm and 30 °C for 3 h to 5 h to OD=0.6-0.9.

(3) All bacterial solutions were placed in a 50 mL centrifuge tube on ice for 15 min, and centrifuged at 4,000 rpm and 4 °C for 10 min.

(4) The bacterial cells were fully suspended in about 30 mL of pre-cooled 10% glycerol, and centrifuged at 4,000 rpm and 4 °C for 10 min.

(5) The bacterial cells were washed twice with pre-cooled 10% glycerol.

(6) The cells were resuspended in 400 μL of pre-cooled 10% glycerol, aliquoted into 1.5 mL centrifuge tubes, 80 μL per tube, and stored at −70 °C or subjected to click transformation.

2) Plasmid electroporation: approximately 1 μg of plasmid was added to 80 μL of competent cells, mixed well, transferred to a 1 mm electroporation cup, and immediately added into a 1.5 mL EP tube with a medium containing 1 mL of BHIS (preheated at 46 °C) after electroporation at 1.8 kV, and then transferred to a metal bath at 46 °C for 6 min. The bacterial cells were cultured on a shaker at 30 °C for 1 h to 2 h, an appropriate amount of the cells was spread on the LBHIS solid medium plate containing the corresponding resistance, and cultured statically at 30 °C for 2 d to 3 d until a single colony grew.

The BHI medium included: brain heart infusion 37 g/L, $(NH_4)_2SO_4$ 10 g/L, $K_2HPO_4$ 0.2 g/L, $NaH_2PO_4$ 0.3 g/L, and $MgSO_4$ $7H_2O$ 0.5 g/L, pH=7.2.

The LBHIS medium included: peptone 5 g/L, NaCl 10 g/L, yeast powder 2.5 g/L, brain heart infusion 18.5 g/L, and sorbitol 91.1 g/L.

1.3.4. Preparation and transformation of *Saccharomyces cerevisiae* competent cells Preparation of *Saccharomyces cerevisiae* Competent Cells:

(1) A fresh single clone of *Saccharomyces cerevisiae* EBY100 was selected from the YPD plate into 10 mL YPD liquid medium, and cultured overnight at 30 °C and 250 rpm.

(2) The overnight culture was determined to be $OD_{600}$=3.0-5.0.

(3) 10 mL of YPD overnight culture was diluted to $OD_{600}$=0.2-0.4.

(4) The culture was continued to be cultured in a shaker at 28 °C to 30 °C for 3 h to 6 h to $OD_{600}$=0.6-1.0.

(5) After centrifugation at room temperature and 1,500 g for 5 min, the yeast cells were collected while a supernatant was discarded.

(6) The yeast cells were washed with 10 mL of washing solution, then centrifuged at room temperature and 1,500 g for 5 min to collect the cells and discard the supernatant.

(7) The yeast cells were resuspended with 1 mL of TE/LiAc to 50 μL per tube.

Transformation of *Saccharomyces cerevisiae* Competent Cells:

(1) 2 μL each of the plasmids to be transfected was added separately to 50 μL of competent cells and mixed well.

(2) 500 μL of transformation solution (PEG/LiAc, dimethyl sulfoxide) was added and mixed evenly by flicking on the tube wall.

(3) The cells were placed in a 30 °C water bath for 1 h, and mixed evenly by flicking on the tube wall every 15 min.

(4) 1 mL of YPD medium was added and incubated on a shaking table at 30 °C for 1 h.

(5) Centrifugation was conducted at 3,500 g for 5 min, a precipitate was remained while discarding the supernatant.

(6) The precipitate was resuspended in 150 μL of TE and applied to a corresponding SD plate; the SD plate was placed upside down and cultured at 30 °C.

1.4. Vector construction:

The synthesized gRNA was ligated into the vector pgRNA according to a method in "*Molecular Biology Experimental Technology*" to form gRNA expression vectors, which were named as ppc-pgRNA, gpd-pgRNA, gpp-gRNA, bmsq-gRNA, pgsq-gRNA, scsq-gRNA, and glnA-gRNA in sequence.

A construction method was as follows (taking ppc-pgRNA as an example): a DNA fragment at position +465 of the CDS interval of artificially-synthesized phosphoenolpyruvate carboxylase gene with EcoRI and NheI enzyme cleavage sites (ppc, NC_000913.3) was digested with restriction endonucleases EcoRI and NheI and then gel recovered, while the pgRNA vector was also digested and gel recovered using restriction endonucleases EcoRI and NheI. The DNA fragment at the +465 position of the CDS interval of the phosphoenolpyruvate carboxylase gene (ppc, NC_000913.3) after digestion and the pgRNA vector were ligated using T4 ligase. An obtained ligation product was mixed with the competent cells of a receptor strain *E. coli* Top10, placed on ice for 30 min, and heat shocked at 42 °C for 90 s. 400 μL LB liquid medium was added, resuscitated at 37 °C and 160 rpm for 45 min, spread on LB solid medium containing 50 μg/mL kanamycin, and cultured at 37 °C overnight. A recombinant plasmid was selected and subjected to double enzyme digestion and sequencing verification to obtain a ppc-pgRNA recombinant plasmid. In a same way, the recombinant vectors of gpd-pgRNA, gpp-gRNA, bmsq-gRNA, pgsq-gRNA, scsq-gRNA, glnA-gRNA, and ArbP protein vector pCarbP were constructed.

1.4.1. Co-transformation of vectors 1.4.1.1. *E. coli* experiment: 1 μL each of pCarbP and ppc-pgRNA were mixed with *E. coli* competent cells, placed on ice for 3 min, heat-shocked at 42 °C for 90 s, added into 500 μL of LB liquid medium, resuscitated at 37 °C and 150 rpm for 45 min, centrifuged, and spread on a LB solid medium containing tetracycline and ampicillin resistance.

1.4.1.2. *Saccharomyces cerevisiae* experiment: 2 μL each of pCarbP and (gpd-pgRNA/gpp-gRNA) was added to 50 μL of competent cells and mixed well; 500 μL of transformation solution (PEG/LiAc, dimethyl sulfoxide) was added and mixed evenly by flicking on the tube wall; the tube was placed in a 30 °C water bath for 1 h, and mixed evenly by flicking on the tube wall every 15 min; 1 mL YPD medium was added and incubated on a shaking table at 30 °C for 1 h; centrifugation was conducted at 3,500 g for 5 min, a precipitate was remained while discarding the supernatant; the precipitate was resuspended in 150 μL TE and applied to a corresponding SD plate; the SD plate was placed upside down and incubated at 30 °C.

1.4.1.3. *Bacillus subtilis* experiment: the *Bacillus subtilis* strain stored at −80 °C was melted naturally on ice; after melting, 100 ng each of pCarbP and (bmsq-gRNA/pgsq-gRNA/scsq-gRNA) was added, and then electric shock was conducted after 5 min of ice bath; a system in step (1) was transferred to a 0 °C pre-cooled electric shock cup (1 mm), and subjected to electric shock with an electrorotator (at voltage 20 kV/cm, capacitance 25 μF, and resistance 200Ω, conducting 1 time for 5 ms); after the electric shock conversion was completed, heat shock was conducted at 30 °C for 5 min; 1 mL of RM medium was added and the cells were incubate at 37 °C for 3 h to 6 h, then spread on an LB plate containing tetracycline and ampicillin resistance.

1.4.1.4. L-glutamic acid-producing *Corynebacterium glutamicum* experiment: about 1 μg each of pCarbP and glnA-gRNA was added to 80 μL of competent cells, mixed well, transferred to a 1 mm electroporation cup, and immediately added into a 1.5 mL EP tube with a medium containing 1 mL of BHIS (preheated at 46 °C) after electroporation at 1.8 kV, and then transferred to a metal bath at 46 °C for 6 min. The bacterial cells were cultured on a shaker at 30 °C for 1 h to 2 h, an appropriate amount of the cells was spread on the LBHIS solid medium plate containing tetracycline and ampicillin resistance, and cultured statically at 30 °C for 2 d to 3 d until a single colony grew.

1.5. PRM-based targeted mass spectrometry (MS)

Determination of glycerol-3-phosphate dehydrogenase, glycerol-3-phosphatase, glycerol dehydratase, and alanine dehydrogenase in *E. coli* was conducted by a PRM-based targeted mass spectrometry (MS) method; the *Bacillus subtilis* included 4 squalene synthases (SQS): BaSQS, BmSQS, PgSQS and ScSQS genes; the *Corynebacterium glutamicum* included protein expression of AAR (acyl ACP reductase) and ADO (aldehyde-deformylating oxygenase).

Each sample was ground to a powder in liquid nitrogen and resuspended in a lysis buffer containing 50 mM Tris-HCl, 7 M urea, 2 M thiourea, and 1× protease inhibitor (pH=8), along with 10 mM ice-cold acetic acid and 1,4-dimercaptopropanol (DTT). The suspension was incubated at −20 °C for 2 h and centrifuged at 13,000 g and 4 °C for 20 min. The precipitated pellet was resuspended with 10 mM ice-cold acetic acid and DTT and centrifuged again at 13,000 g and 4 °C for 20 min. The precipitated particles were collected and lysed using lysis buffer. The protein was quantified using a Bradford method. The protein was diluted 5-fold by adding 100 mM triethylammonium bicarbonate and digested using trypsin (Promega, USA) at a substrate-to-enzyme ratio of 50:1 (w/w). Peptides were desalted using a Strata-X C18 column (Phenomenex Inc, California, USA) and then dried using a vacuum centrifuge and frozen at −80 °C until further analysis.

PRM detection was conducted using a Triple TOF 5600+ LC-MS/MS system (SCIEX, Framingham, MA, USA). It was worth noting that the resolution of MS1 scans and associated precursor ions was approximately 35,000, while the resolution of MS/MS scans and associated fragment ions was approximately 15,000 (PRM transitions). The MS/MS spectra of the 30 most abundant precursor ions were obtained using data-dependent acquisition. In each cycle (250 ms), a 50 ms/MS/MS spectrum was obtained after each measurement of MS1 scan, with a total cycle time of 1.8 s. The acquired PRM included MS1 scan (250 ms) and target MS/MS scan (cycle time 1.3 s to 3.3 s).

All observed peptides were entered into Skyline software, and peptides for protein quantification were selected based on ion signals in the spectral library. The relevant peptides with retention times and m/z values were exported using Skyline software, and then input into the MS control software Analyst (version 1.7, SCIEX, USA) to construct a PRM acquisition method. A final PRM acquisition method used a quadrupole tandem time-of-flight mass spectrometer (TripleTOF 5600+ system, SCIEX, USA) to collect data from all samples. Typically, precursor ions were selected with a quadrupole and then fragmented, and the fragment ions were quantitatively determined by a TOF mass spectrometer. To eliminate protein cross-contamination, “blanks” were run between adjacent samples to flush the column. The data were then processed using Skyline, followed by manual inspection of the quantification results for the peptides in the target protein.

1.6. Two-plasmid system for evaluating target regulation of Arbp-related sRNAs

*A. dieselolei* B5 ArbP-related sRNAs were evaluated for regulation by target mRNAs using the *E. coli* system proposed by Urban and Vogel according to previously published protocols. Considering plasmids expressing diverse ArbP-related sRNAs in the PL promoter, genes encoding ArbP-related sRNAs were amplified by PCR and the arbP gene was continuously expressed following a previously published protocol. In this study, translated GFP fusions with ArbP-related potential sRNA target genes were established using gDNA-amplified PCR products as previously described. The fusions were inserted using NheI/BfrBI restriction enzyme digestion and then ligated into a pXG10 plasmid backbone. The DNA sequence was analyzed to verify the authenticity of the construction. The target gfp fusion plasmid was transfected into *E. coli* TOP10 cells (Invitrogen), and then transfected alone or in combination with sRNA expression plasmid.

Fluorescence assay was conducted to measure GFP levels. An LB medium (2 mL) containing chloramphenicol and ampicillin was added to a single bacterial colony incubated at 37 °C and 220 rpm for 12 h. A volume of culture medium equivalent to OD600/mL was mixed with phosphate-buffered saline (PBS) at pH=7.4 containing 4% formaldehyde (1 mL), and centrifuged at 7,500 g for 2 min. 1 mL of 1×PBS was added to resuspend the cell pellet. For flow cytometry analysis, a 1/1000 dilution of 1×PBS was prepared to conduct measurements on a BD FACS Calibur instrument. Three replicate experiments were set up for different samples. Results were analyzed using Cyflogic software.

Example 2: Effect of the AbrP Protein Translation-Promoting System of *Alcanivorax* in *E. coli*

Figure 6A:
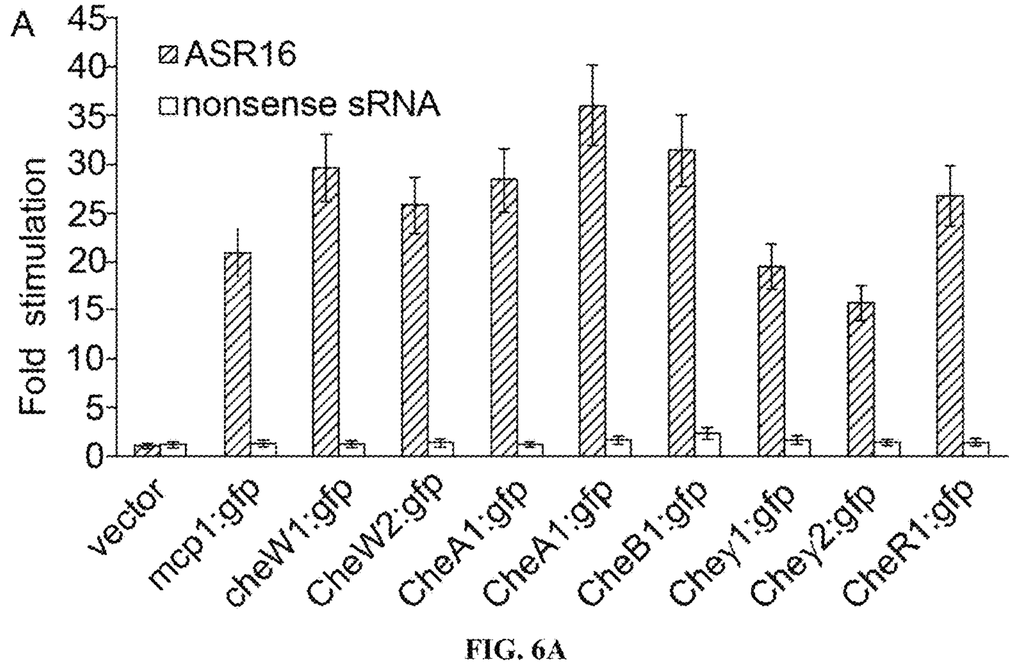
FIGS. 6A-C show gene results of post-transcriptional regulation of *Alcanivorax* non-coding sRNA (ASR)16 (A), ASR50 (B), and ASR161 using a modified two-plasmid system; where the *Alcanivorax* small non-coding RNA (ASR)16(A), ASR50(B), and ASR161 are regulated post-transcriptionally using the modified two-plasmid system; a fluorescence intensity of *E. coli* strains carrying gene-specific reporter genes and control plasmids is separately set to 1; and a bar graph represents mean±standard deviation of biologically independent replicates (n=5), small nonsense RNA: ASR576.
Figure 6B:
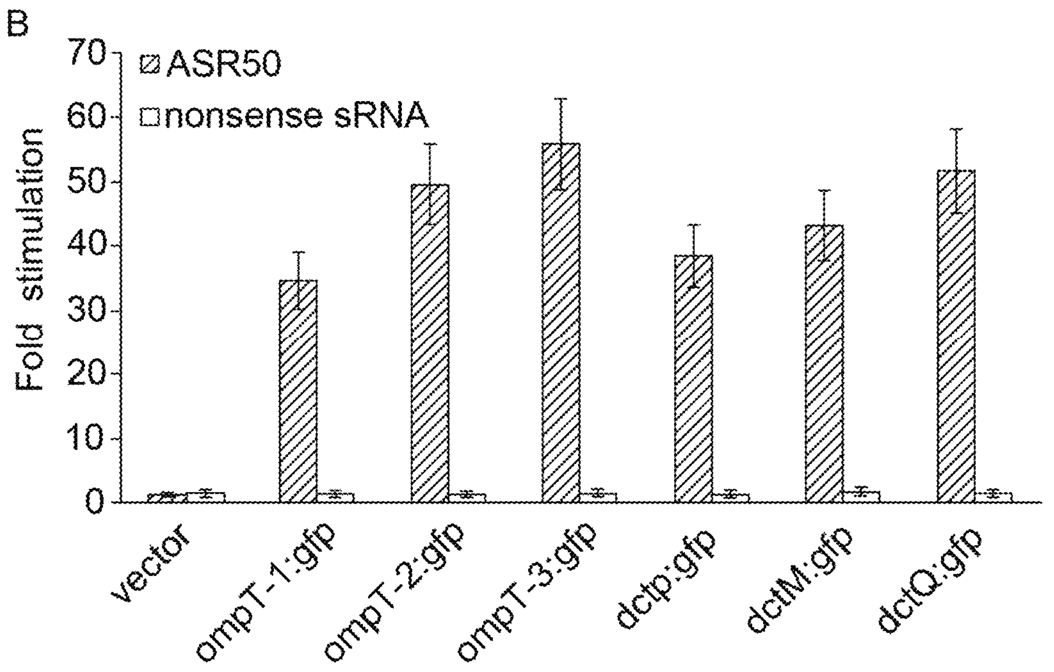
Figure 6C:
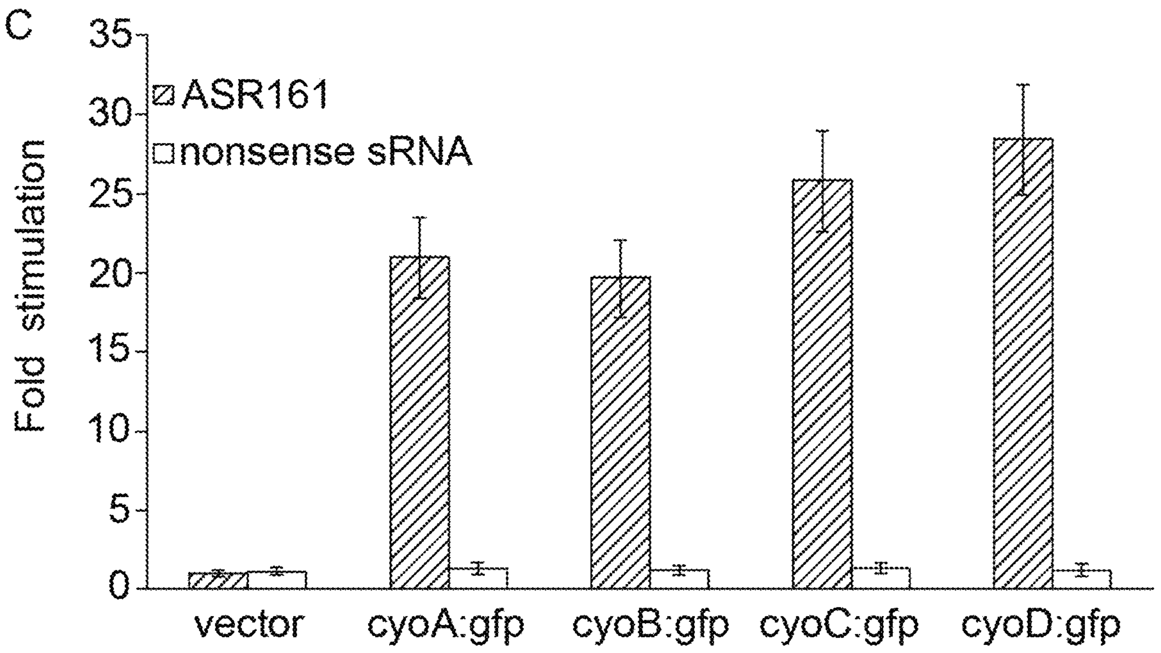
Figure 7A:
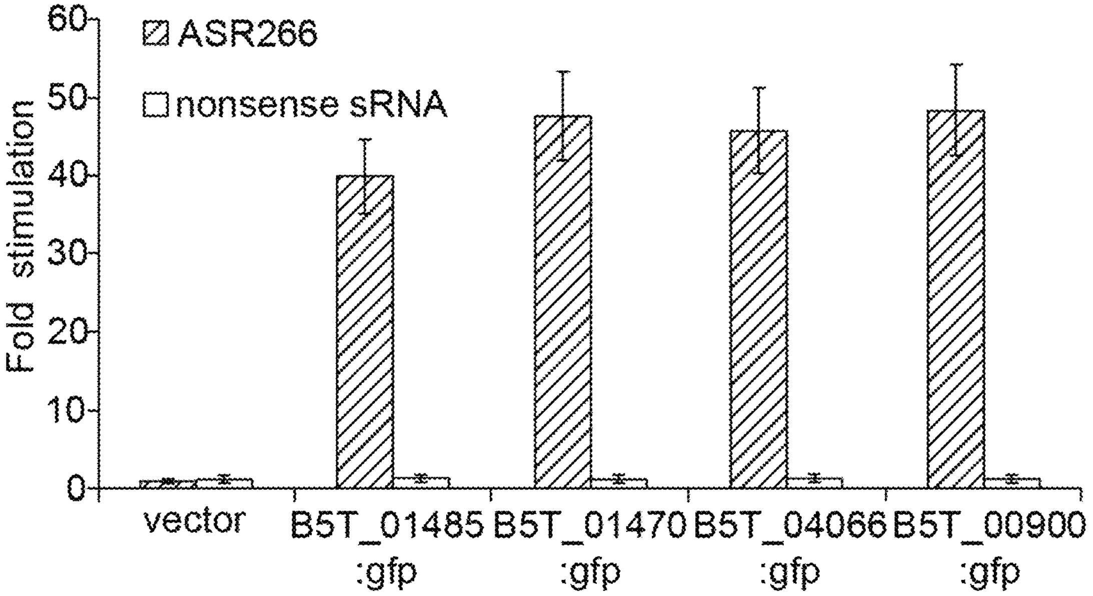
FIGS. 7A-D show the gene translation levels of wild-type B5 strain and small RNA mutant strain in n-alkanes detected by parallel reaction monitoring (PRM); where *Alcanivorax* non-coding small RNA (ASR)16 mutant strain SRB5-16; SRB5-50, ASR50 mutant strain; SRB5-161, ASR161 mutant strain; SRB5-266, ASR266 mutant strain; SRB5-285, ASR285 mutant strain; SRB5-434, ASR434 mutant strain; ASR640 mutant strain SRB5-640.
Figure 7B:
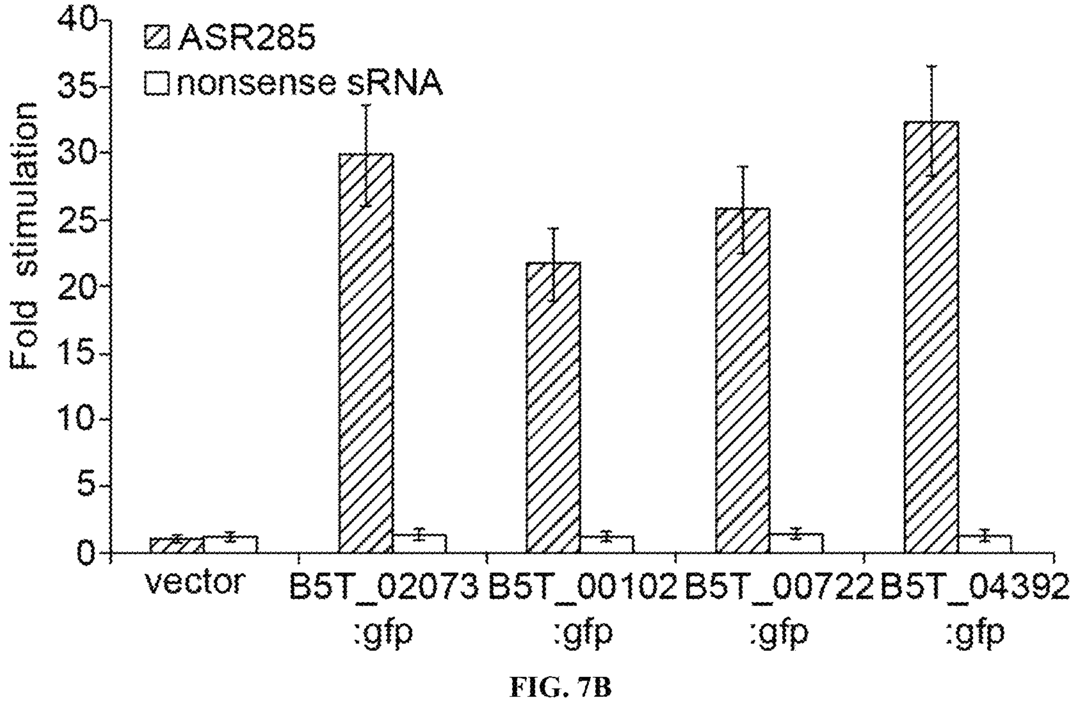
Figure 7C:
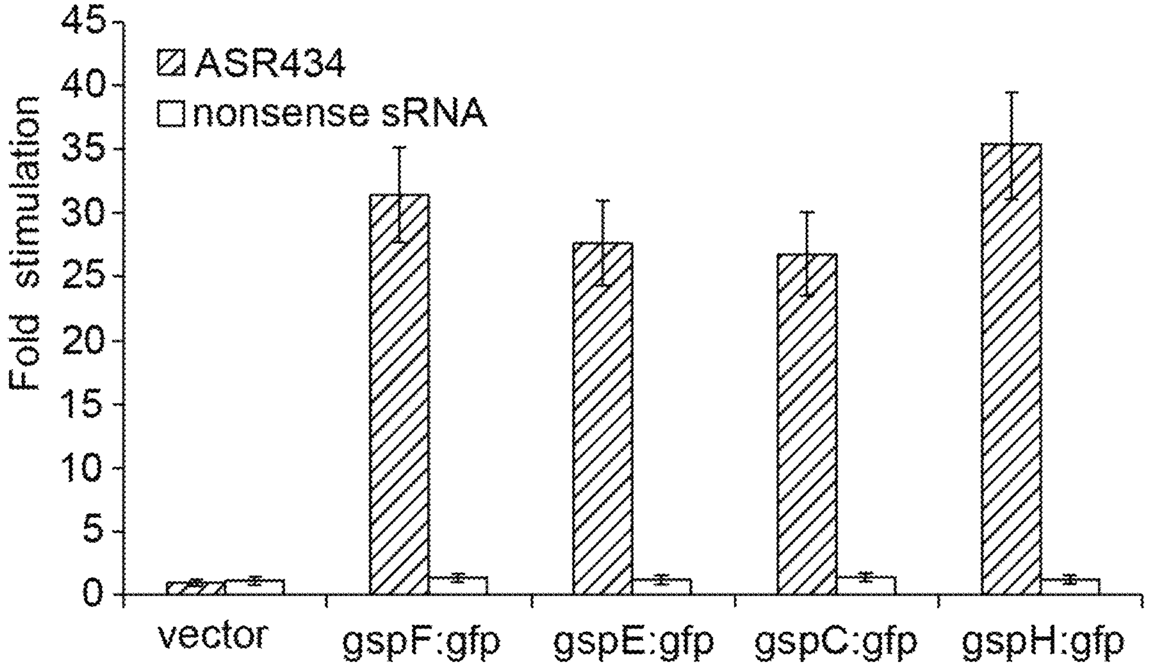
Figure 7D:
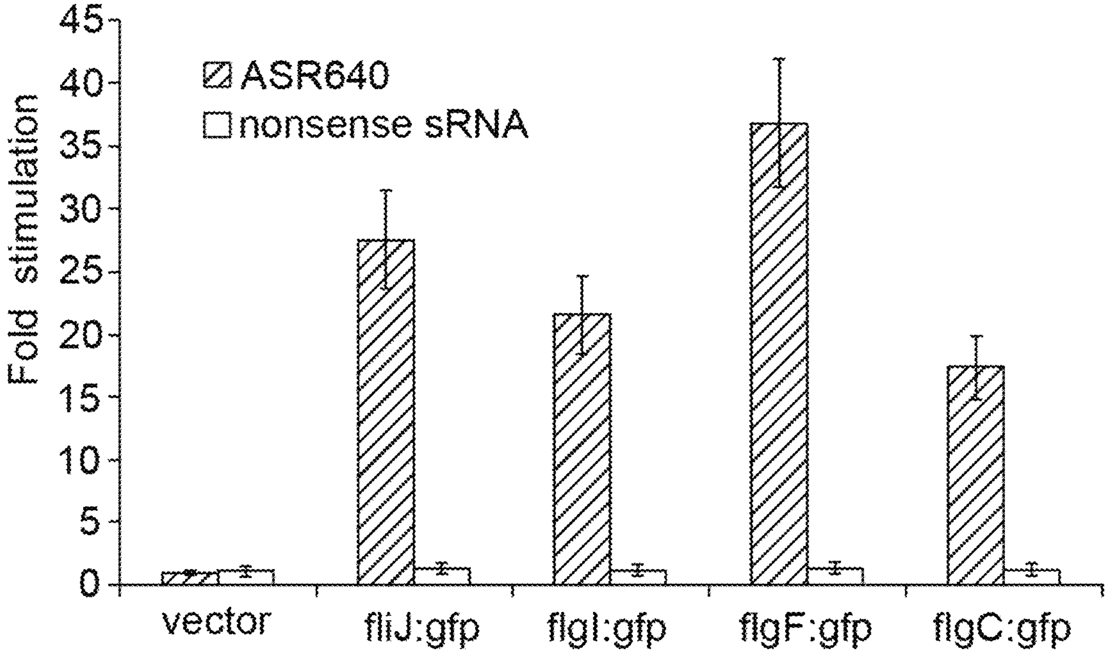

In order to study the regulatory mechanism of Arbp-related gene expression mediated by sRNAs, a modified *E. coli* two-plasmid system was used. The two-plasmid system could continuously express B5 ArbP protein to regulate the expression of ArbP-related sRNA and target translation fusion. The target transcript containing the ArbP-associated sRNA binding site was selected and fused to superfolded green fluorescent protein (sfgfp). The fusion activity of the reporter gene was assessed by monitoring GFP fluorescence over time. The potential sRNA target GFP gene reporter plasmid and the sRNA overexpression vector were co-transfected into *E. coli*; and the ArbP-related sRNA targets were activated post-transcriptionally (FIGS. 6A-C and FIGS. 7A-D). In particular, 8 target fusions (mcp1, cheW1, cheW2, cheA1, cheB1, cheY1, cheY2, and cheR1) were strongly activated in *E. coli* cells co-expressing ASR16 and B5 ArbP (FIGS. 6A-C), indicating that ASR16 played a role in the post-transcriptional regulation of these mRNAs. Likewise, the regulation of OmpT-1::gfp, OmpT-2::gfp, OmpT-3::gfp, DctP::gfp, DctM::gfp, and DctQ::gfp fusions was entirely dependent on ArbP-related ASR50 sRNA in *E. coli* (FIGS. 6A-C). When ASR161 and B5 ArbP were coexpressed, GFP fluorescence increased approximately 5- to 10-fold above the target fusion plasmid control (CyoA::gfp, CyoB::gfp, CyoC::gfp, and CyoD::gfp), indicating that ASR161 strongly activated the translation of these mRNAs in *E. coli* (FIGS. 6A-C).

To further evaluate the impact of ArbP-related sRNAs on translational regulation, PRM was conducted to determine the protein expression levels of target genes. Compared with the wild-type strain, the protein expression levels of all target genes in the sRNA mutant strain were down-regulated (fold 0.24 to 0.03). Therefore, sRNA related to ArbP had an impact on the translational regulation of sRNA target genes, but showed a low regulatory activity on target mRNA.

Example 3: Use of the AbrP Protein Translation-Promoting System in Bacteria in Cell Factory for Metabolic Engineering of *E. coli*

Figure 8:
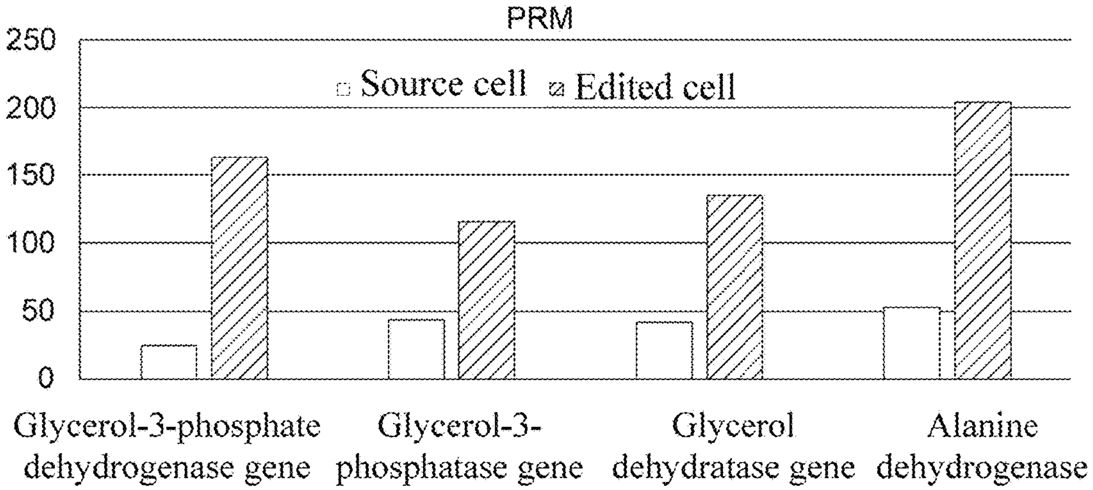
FIG. 8 shows a gene PRM measurement diagram of source cells and edited cells of *E. coli;*

The expression levels of the target proteins in the source cells of *E. coli* and the editing cells obtained by co-transformation with the AbrP protein translation-promoting system were compared, thereby studying the regulatory role of the AbrP protein translation-promoting system in cell factory for metabolic engineering of *E. coli*. The protein expression levels of the target genes in each cell were detected through the PRM-based targeted mass spectrometry method (Method 1.5). The results showed that compared with the source cells, the protein expression levels of the target genes (glycerol-3-phosphate dehydrogenase, glycerol-3-phosphatase, glycerol dehydratase, and alanine dehydrogenase) in edited *E. coli* cells (by PRM) were significantly increased. The glycerol-3-phosphate dehydrogenase had a 6.65-fold increase in protein level, the glycerol-3-phosphatase had a 2.68-fold increase in protein level, the glycerol dehydratase had a 3.21-fold increase in protein level, the alanine dehydrogenase had a 3.84-fold increase in protein level (FIG. 8).

Example 4: Use of the AbrP Protein Translation-Promoting System in Bacteria in Cell Factory for Metabolic Engineering of *Bacillus subtilis*

Figure 9:
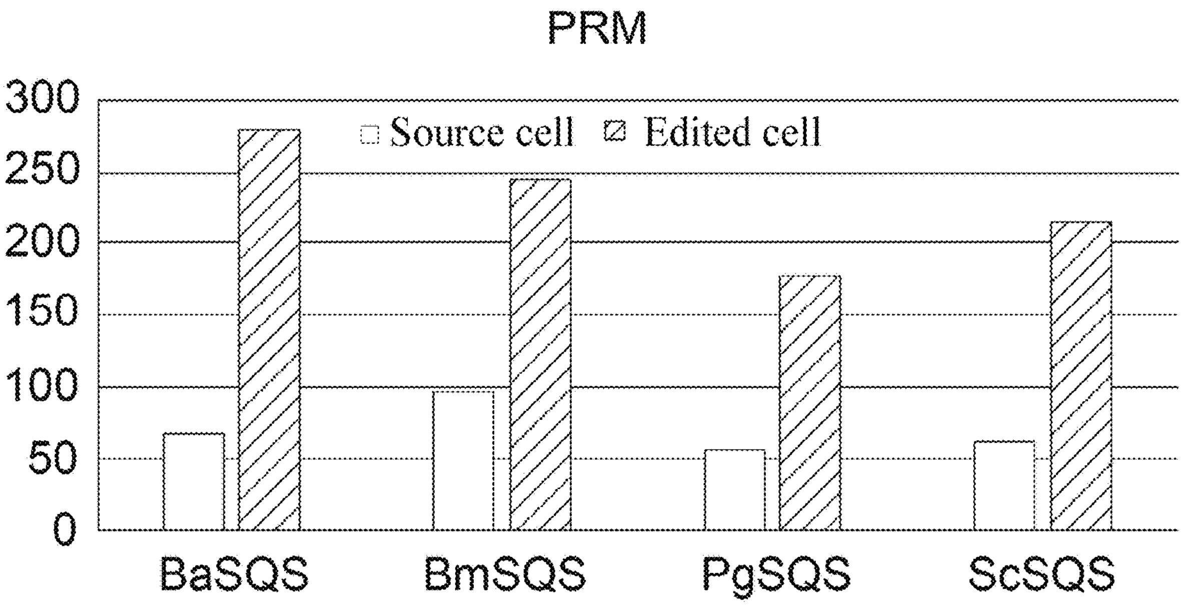
FIG. 9 shows a gene PRM measurement diagram of source cells and edited cells of *Bacillus subtilis*, where BaSQS: squalene synthase BaSQS; BmSQS: squalene synthase BmSQS; PgSQS: squalene synthase PgSQS; ScSQS: squalene synthase ScSQS.

The expression levels of the target proteins in the source cells of *Bacillus subtilis* and the editing cells obtained by co-transformation with the AbrP protein translation-promoting system were compared, thereby studying the regulatory role of the AbrP protein translation-promoting system in cell factory for metabolic engineering of *Bacillus subtilis*. The protein expression levels of the target genes in each cell were detected through the PRM-based targeted mass spectrometry method (Method 1.5). The results showed that compared with the source cells, the protein expression levels (by RPM) of the target genes (4 squalene synthases: BaSQS, BmSQS, PgSQS, and ScSQS) in the edited *Bacillus subtilis* cells were significantly increased. The BaSQS had a 4.12-fold increase in protein level, the BmSQS had a 2.54-fold increase in protein level, the PgSQS had a 3.14-fold increase in protein level, the ScSQS had a 3.49-fold increase in protein level (FIG. 9).

Example 5: Use of the AbrP Protein Translation-Promoting System in Bacteria in Cell Factory for Metabolic Engineering of *Corynebacterium glutamicum*

Figure 10:
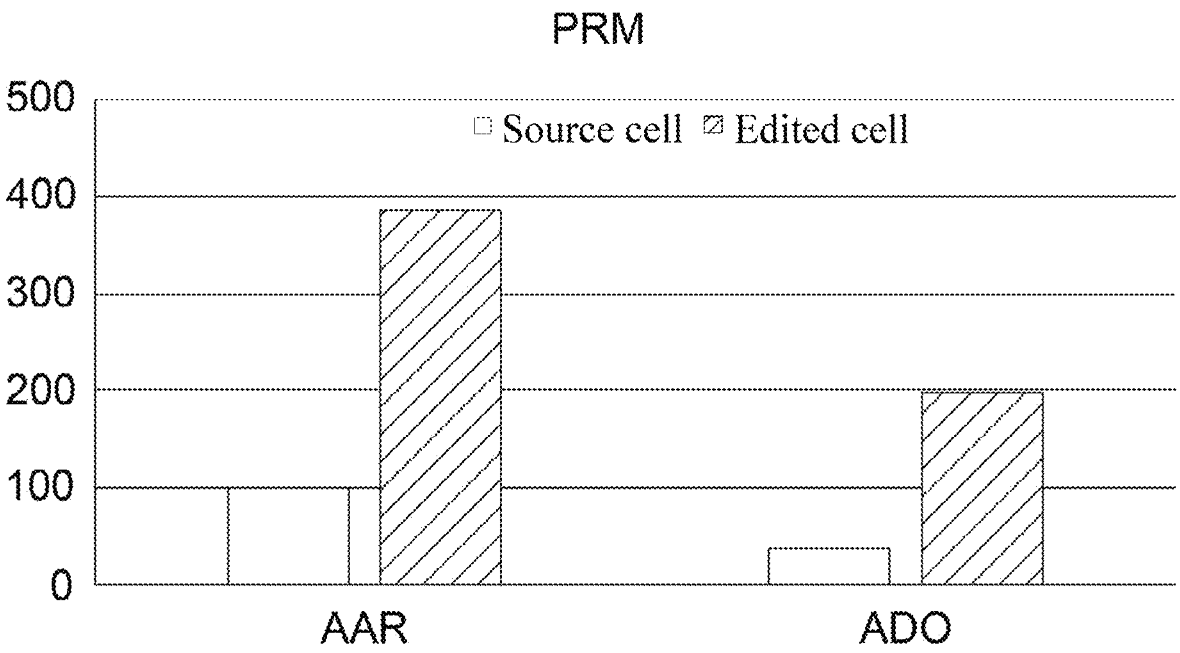
FIG. 10 shows a gene PRM measurement diagram of source cells and edited cells of *Corynebacterium glutamicum*, where AAR: cyanobacterial acyl-(acyl carrier protein (ACP)) reductase; ADO: cyanobacterial aldehyde-deformylating oxygenase.

The expression levels of the target proteins in the source cells of *Corynebacterium glutamicum* and the editing cells obtained by co-transformation with the AbrP protein translation-promoting system were compared, thereby studying the regulatory role of the AbrP protein translation-promoting system in cell factory for metabolic engineering of *Corynebacterium glutamicum*. The protein expression levels of the target genes in each cell were detected through the PRM-based targeted mass spectrometry method (Method 1.5). The results showed that compared with the source cells, the protein expression levels (by RPM) of the target genes (AAR: acyl ACP reductase, ADO: aldehyde-deformylating oxygenase) in the edited *Corynebacterium glutamicum* cells were significantly increased. The AAR had a 3.88-fold increase in protein level, the ADO had a 5.20-fold increase in protein level (FIG. 10).

Although the above example has described the present disclosure in detail, it is only apart of, not all of, the examples of the present disclosure. Other examples may also be obtained by persons based on the example without creative efforts, and all of these examples shall fall within the protection scope of the present disclosure.

What is claimed is:

1. A method of promoting recombinant protein translation in a host cell, comprising introducing into the host cell a first polynucleotide encoding an RNA-binding protein AbrP and a second polynucleotide encoding a guide RNA (gRNA), wherein the AbrP comprises the amino acid sequence of SEQ ID NO: 1, the gRNA is selected from the group consisting of SEQ ID NOs: 5-11, the host cell is selected from the group consisting of *Escherichia coli, Bacillus subtilis, Corynebacterium glutamicum*, and *Saccharomyces cerevisiae,* and wherein the recombinant protein is selected from the group consisting of phosphoenolpyruvate carboxylase (PPC), glycerol-3-phosphate dehydrogenase (GPD), glycerol-3-phosphate phosphatase (GPP), squalene synthasei (SQS), and glutamine synthetase (GlnA).

2. The method according to claim 1, wherein the recombinant protein is an exogenous protein.

3. A method of metabolic engineering regulation of a prokaryotic cell, comprising introducing into the prokaryotic cell a first polynucleotide encoding an RNA-binding protein AbrP and a second polynucleotide encoding a guide RNA (gRNA), wherein the AbrP comprises the amino acid sequence of SEQ ID NO: 1, the gRNA is selected from the group consisting of SEQ ID NOs: 5-11, the prokaryotic cell is selected from the group consisting of *Escherichia coli, Bacillus subtilis*, and *Corynebacterium glutamicum,* and wherein the metabolic engineering regulation comprises increasing the expression of a protein selected from the group consisting of phosphoenolpyruvate carboxylase (PPC), glycerol-3-phosphate dehydrogenase (GPD), glycerol-3-phosphate phosphatase (GPP), squalene synthasei (SQS), and glutamine synthetase (GlnA).

4. The method according to claim 3, wherein the protein is an exogenous protein.

5. A method of metabolic engineering regulation of a eukaryotic cell, comprising introducing into the prokaryotic cell a first polynucleotide encoding an RNA-binding protein AbrP and a second polynucleotide encoding a guide RNA (gRNA), wherein the AbrP comprises the amino acid sequence of SEQ ID NO: 1, the gRNA is selected from the group consisting of SEQ ID NOs: 6 and 7, the eukaryotic cell comprises *Saccharomyces cerevisiae,* and wherein the metabolic engineering regulation comprises increasing the expression of a protein selected from the group consisting of glycerol-3-phosphate dehydrogenase (GPD), and glycerol-3-phosphate phosphatase (GPP).

* * * * *